United States Patent [19]

Dunn et al.

[11] Patent Number: 4,975,271
[45] Date of Patent: Dec. 4, 1990

[54] MUSCOSAL DELIVERY SYSTEMS FOR TREATMENT OF PERIODONTAL DISEASE

[75] Inventors: Richard L. Dunn; Kenneth C. Godowski, both of Fort Collins; Ronald J. Harkrader, Louisville; George L. Southard, Fort Collins, all of Colo.

[73] Assignee: Vipont Pharmaceutical, Inc., Fort Collins, Colo.

[21] Appl. No.: 286,651

[22] Filed: Dec. 19, 1988

[51] Int. Cl.$^5$ ................................................. A61K 7/16
[52] U.S. Cl. ........................................ 424/49; 424/54; 424/58; 514/708; 514/900; 514/901; 514/902; 514/946; 514/947
[58] Field of Search .......................... 424/49, 54, 58; 514/708, 900, 901, 902, 946, 947

[56] References Cited

U.S. PATENT DOCUMENTS

| | | | |
|---|---|---|---|
| 3,549,770 | 12/1970 | Herschler et al. | 514/708 |
| 3,743,727 | 7/1973 | Herschler | 514/708 |
| 3,758,689 | 9/1973 | Rapfogel | 514/900 |
| 4,039,664 | 8/1977 | Stoughton et al. | 514/947 |
| 4,405,616 | 9/1983 | Rajadhyaksha | 514/947 |
| 4,517,172 | 5/1985 | Southard | 424/195.1 |
| 4,557,934 | 10/1985 | Cooper | 514/947 |
| 4,683,133 | 7/1987 | Southard | 514/902 |
| 4,689,216 | 8/1987 | Greene | 424/58 |
| 4,767,861 | 8/1988 | Boulware | 546/48 |
| 4,769,452 | 9/1988 | Boulware | 546/48 |
| 4,818,533 | 4/1989 | Boulware et al. | 514/280 |

FOREIGN PATENT DOCUMENTS

| | | | |
|---|---|---|---|
| 3274M | 4/1965 | France | 514/708 |
| 61130210 | 6/1986 | Japan | 514/900 |
| 61148125 | 7/1986 | Japan | 514/900 |
| 936916 | 6/1982 | U.S.S.R. | 424/366 |
| 1191082 | 11/1985 | U.S.S.R. | 514/902 |

OTHER PUBLICATIONS

Thorne et al., J. Soc. Cosmet. Chem., 37:279–286, Jul.-/Aug. 1986, Janguinarine in Oral Health Care Producers.
Tolkachev CA. 84:105861u (1976).
Barry CA.103:220677m (1985), Barry CA. 108:81981u (1988).
Hoelgard CA 108:226759Q (1988).
Sasaki CA 109:98649k (1988).
Nishigaki CA.109:237061c (1988).

*Primary Examiner*—Shep K. Rose
*Attorney, Agent, or Firm*—Merchant, Gould, Smith, Edell, Welter & Schmidt

[57] ABSTRACT

A muscosal delivery system is provided for use in treating periodontal disease. The system is composed of a chemotherapeutic agent dissolved in a skin-penetration enhancer. The solution of chemotherapeutic agent and skin-penetration enhancer is placed into the periodontal pocket where the agent is transported into the surrounding gingival tissue by means of the penetration enhancer.

8 Claims, No Drawings

MUSCOSAL DELIVERY SYSTEMS FOR TREATMENT OF PERIODONTAL DISEASE

BACKGROUND OF THE INVENTION

Periodontal disease or gum disease as it is often called can be defined as an infection and inflammation of the gingiva or gums and loss of underlying alveolar bone support. There are varying levels of severity of the disease with the mildest cases termed as gingivitis (inflamed and bleeding gums). More severe cases are clinically known as periodontitis and can involve loss of bone support. Gingivitis is reversible and can often be eliminated with a thorough dental prophylaxis followed by improved personal oral hygiene procedures. If gingivitis is not controlled, the disease often progresses into periodontitis.

Periodontitis is not only characterized by bacterial infection and inflammation, it is also accompanied by the formation of periodontal pockets (spaces between the teeth and gums) and bone deterioration which can lead to tooth loss. Periodontitis is recurring, progressive, and episodic. There is no cure at this time. Effective treatment is to apply professional intervention to halt disease progression.

Professional intervention may involve surgical or nonsurgical procedures. Nonsurgical treatment consists of periodic professional scaling, root planing, and soft tissue curettage, in combination with conscientious home care by brushing and flossing on the part of the patient. Surgical treatment involves gingivectomy and flap surgery to recontour the soft and hard tissue around the diseased areas.

In recent years, it has become increasingly recognized that control of periodontitis may be possible with the use of antimicrobial agents delivered to the infected site. Systemic antibiotics taken orally or intramuscularly have been successfully used, but due to the concern about allergic responses, the development of resistance, and the treatment of the whole person rather than the specific infection site, their use is recommended only in the severest of periodontal cases.

One of the most recently proposed methods of treating periodontitis with chemotherapeutic agents has involved the placement of these agents in conjunction with polymeric delivery systems directly into the periodontal pocket. These include the cellulose hollow fibers loaded with tetracycline described in U.S. Pat. No. 4,175,326 to Goodson, the ethylcellulose films loaded with metronidazole described in U.S. Pat. No. 4,568,535 to Loesche, the absorbable putty-like material described in U.S. Pat. No. 4,568,536 to Kronenthal, the ethylene vinyl acetate fibers loaded with tetracycline described in the European patent application No. 84401985.1 to Goodson, and the biodegradable microspheres and matrix described in U.S. Pat. No. 4,685,883 to Jernberg.

All of these delivery systems involve placing the product directly into the periodontal pocket and having the chemotherapeutic agent released over a time of 5 to 14 days. Because most of the chemotherapeutic agents are potent antimicrobials or antibiotics, a brief exposure at even low concentrations is sufficient to destroy any periodontal pathogen in the pocket. However, the irrigation of periodontal pockets with antimicrobial or antibiotic solutions is ineffective in controlling periodontal disease and these agents have to be delivered over a long period of time to be effective. The reason for these observations is that the bacteria responsible for periodontal disease are not all located within the periodontal pocket. If the bacteria are located within the gingival tissue as well as the pocket, then the local application of an antimicrobial will destroy the bacteria within the pocket and on the surface of the gingival tissue but not that deep within the tissue. The gingival tissue on the surface dies and is replaced with fresh tissue within a time of approximately one week. Thus, fresh tissue infected with bacteria not killed with the original treatment will repopulate the pocket and the disease continues to progress. The polymeric controlled delivery systems are effective because they continue to release the chemotherapeutic agent over a long time and prevent the repopulation of the pocket by killing the freshly exposed bacteria.

Recent research has indeed shown that the bacteria often responsible for periodontal disease exist not only in the periodontal pocket but also within the gingival tissue. This is especially true for localized juvenile periodontitis. The only way to treat this form of periodontal disease has been to administer systemic antibiotics which can attack the bacterial infection within the gingival tissue itself. Several researchers have also shown that the bacteria responsible for periodontal disease have been found in the tissue of patients with normal adult periodontitis. Thus, there is a need for a local delivery system that allows chemotherapeutic agents to destroy the bacteria within the gingival tissue as well as the periodontal pocket.

Although the polymeric controlled delivery systems placed within the periodontal pocket have been shown to be effective in treating periodontal disease, they have several problems which hinder their widespread use. Most of these systems have been fibers, films, or sponges which are difficult and time-consuming to place into the contours of a periodontal pocket. Any material exposed above the gingival margin is quickly removed by normal oral hygiene procedures such as brushing or flossing. Moreover, unless the delivery systems are adhesively bound to the tooth or the gingival tissue, they tend to be expelled from the pocket by the mechanical action of the teeth and gums during eating or by the outward flow of the gingival crevicular fluid.

One method to avoid the placement and retention problems associated with the polymeric delivery systems is to deliver the chemotherapeutic agent by itself to the periodontal pocket. However, treatment by mouth rinse and other topically applied oral medicinal agents does not allow the antibacterial agents to penetrate into the periodontal pocket where they are needed. Irrigation of the pockets with these agents has shown some effects on gingivitis, but the short time of exposure with irrigation solutions and the rapid removal of any therapeutic agent by the outward flow of the crevicular fluid make this type of treatment ineffective with severe cases of periodontitis. The one system that seems to have effectiveness is the placement of an aqueous solution of tetracycline directly into the periodontal pocket. The rationale for the effectiveness of this treatment is the adsorption of tetracycline to dentin at the base of the tooth and the subsequent sustained release over a period of about one week. Thus, tetracycline provides its own controlled release system in this instance. It does not, however, penetrate the gingival tissue to kill the bacteria located intragingivally.

Apparently tetracycline is not alone in its lack of tissue penetration. Other antimicrobials added to the periodontal pocket as aqueous solutions do not penetrate the gingival tissue deep enough to affect the bacteria located within the tissue. There is a need for a delivery system for chemotherapeutic agents that enables the agent to penetrate the gingival tissue layers sufficiently to contact and destroy all periodontal pathogens.

SUMMARY OF THE PRESENT INVENTION

The present invention relates to the use of a mucosal penetration system for the delivery of chemotherapeutic agents (i.e. drug or bioactive agent) to localized sites in the mouth for the treatment of periodontal disease. The method of treatment involves the placement of a chemotherapeutic agent into the periodontal pocket in conjunction with a skin-penetration enhancer that enables the agent to penetrate into the infected gingival tissue.

The term drug or bioactive agent as used herein includes without limitation physiologically or pharmacologically active substances that act locally or systemically in the body. Representative drugs and biologically active agents to be used in this application include antimicrobials, antibiotics, anti-inflammatory agents, anti-infectives, analgesics, tissue and bone growth factors, and the benzophenanthridine alkaloids. To those skilled in the art, other drugs or bioactive agents that can be released into an aqueous environment can be utilized in the described mucosal penetration system. Also, various forms of the drugs or bioactive agents may be used. These include, without limitation, forms such as uncharged molecules, molecular complexes, salts, ethers, esters, amides, etc., which are biologically activated when injected into the body.

The skin-penetration enhancer useful in the practice of this invention can be selected from a list of compounds which have been shown to increase the rate of penetration into tissue of various biologically active agents. These include N-methyl-2-pyrrolidone, 2-pyrrolidone, ethanol, propylene glycol, dimethylformamide, dimethyl sulfoxide, caprolactam, oleic acid, decylmethylsulfoxide, 1-dodecylazacycloheptan-2-one, isopropyl myristate, hexamethylene palmitamide, hexamethylene lauramide, and other aliphatic acids, alcohols, and esters.

The method provided by this invention is to dissolve the chemotherapeutic agent into the skin-penetration enhancer and to place the solution into the infected periodontal pocket. The penetration enhancer will penetrate the mucosal tissue and carry the agent into the tissue where it can contact and destry the bacteria. A preferred method is to use a chemotherapeutic agent that is highly soluble in the skin-penetration enhancer but sparingly soluble in water or body fluids.

In this manner the agent is carried into the tissue as long as it is in contact with the enhancer, but as soon as the enhancer is diluted or carried away by the body fluids the agent is precipitated. The precipitation of the agent as a poorly soluble solid within the tissue provides a controlled delivery system in which the agent is released over a long time because of its low water solubility. However, the agent must have sufficient water solubility to provide a concentration of agent within the tissue that is effective in destroying bacteria or providing the therapeutic action that is desired.

Most antimicrobial or antibiotic agents currently used to treat periodontal disease have been modified to provide high water solubility because they are normally delivered to the body in an aqueous solution. Although the high water solubility allows them to be used in high concentrations, it also causes them to be flushed quickly from the pocket by the gingival crevicular fluid. Their high water solubility also prevents them from penetrating the lipid layers of mucosal tissue.

The same antimicrobials and antibiotics can be modified for use in this invention to give more hydrophobic compounds which are readily soluble in the skin-penetration enhancers. Being more hydrophobic, these compounds are less water soluble and less likely to be flushed out by the gingival crevicular fluid.

As an example, tetracycline is normally used as the water soluble hydrochloride salt. The salt form of the drug allows higher concentrations in the normal aqueous media used for injection of the drug. The free base of tetracycline is less water soluble and more soluble in organic solvents such as those used for skin-penetration enhancement. Also, the formation of salts of tetracycline from organic acids such as acetic, propionic, gluconic, lactic and others tend to give more hydrophobic compounds soluble in the skin-penetration enhancers.

In addition to using the free base or salts of organic acids, the chemotherapeutic agents can be made more hydrophobic by converting them to esters, amides, or other compounds which hydrolyze in the body to give the active agent. An example is the conversion of sanguinarine hydrochloride which is water soluble to the ethoxy ester, ethoxydihydrosanguinarine. This form of the antimicrobial agent has low water solubility, but converts in body fluid to the active and water soluble form. The conversion is dependent upon the pH of the body fluid and the equilibrium which is established. The ethoxy compound is soluble in ethanol, chloroform, N-methyl-2-pyrrolidone and other organic solvents. This compound when dissolved in N-methyl-2-pyrrolidone gives a light brown solution. When applied to human skin or tissue, the solution of drug soaks into the skin to give a clear to slightly tan color at the application site. However, within a time of about 30 minutes, the application site starts to turn orange which is the color of the iminium ion or the active form of the drug. This orange color persists in the skin or tissue for several days before it gradually fades and the drug is removed.

The amount of drug delivered with the mucosal delivery system of this invention depends upon the solubility of the chemotherapeutic agent in the skin-penetration enhancer, the tissue contact time, the depth of penetration, and the quantity of drug needed for efficacy. Depending upon the drug and the particular penetration enhancer, concentrations up to 80% may be possible, however the concentration should be adjusted to give the optimum tissue penetration. If the concentration of drug is too high, then the exposure of the solution to water or body fluids will cause an immediate precipitation of the drug before it has time to penetrate the tissue. Therefore, the concentration of drug and the specific penetration enhancer have to be determined for optimum effect.

Both the amount of drug and the rate of tissue penetration can be determined using two-chamber diffusion cells. The two chambers each with a volume of about 2 mL are separated by a membrane of mucosal tissue. The solution of drug and penetration enhancer is added to the surface of the membrane, each chamber is then filled with phosphate buffered solution, and the entire cell equilibrated at 37° C. in a water bath. Each chamber is stirred. At selected times, aliquots of the receiving fluid in the lower chamber are removed and analyzed for drug. The amount of drug permeating the tissue plotted against time will show the rate of penetration. Using this procedure, the optimum penetration enhancer, the form of the drug, its concentration, and the exposure time can be determined for each chemotherapeutic agent.

DETAILED DESCRIPTION OF EXAMPLES

The following examples are set forth as representative of the present invention. These examples are not to be construed as limiting the scope of the invention as these and other equivalent embodiments will be apparent in view of the present disclosure and accompanying claims.

EXAMPLE 1

Sanguinarine hydrochloride was added to N-methyl-2-pyrrolidone to give a 5% by weight dispersion of the drug in the solvent. The orange-red dispersion was added to human skin to give an orange colored powder after the solvent had dissipated into the skin. The orange powder could then be removed from the skin by wiping or washing with water.

EXAMPLE 2

Ethoxydihydrosanguinarine was added to N-methyl-2-pyrrolidone to give a 5% by weight solution of the drug. The light brown solution was added to human skin where it formed a light brown film which disappeared into the skin within approximately one minute. After about 30 minutes, the area to which the solution had been applied turned an orange color indicative of the iminium form of the drug. The orange color could not be removed from the skin by wiping or washing with water.

EXAMPLE 3

The 5% by weight dispersion of sanguinarine hydrochloride and the 5% by weight solution of ethoxydihydrosanguinarine were added to periodontal pockets in a greyhound dog. The pockets were inflamed and had pocket depths greater than 6 mm. Samples of the bacteria within the pockets were taken prior to treatment and two weeks after treatment. The type of bacteria and the relative percentages were determined. Both materials gave approximately a ten-fold reduction in total bacteria after two weeks. However, the percentage of anerobic bacteria which are normally associated with periodontal disease was reduced from 81% to 31% with the ethoxydihydrosanguinarine solution and remained essentially constant at 88% for the sanguinarine hydrochloride dispersion. The reduction in anerobic bacteria which would be located in the tissue indicates the better penetration of the ethoxydihydrosanguinarine solution into the tissue.

EXAMPLE 4

Ethoxydihydrosanguinarine was dissolved in N-methyl-2-pyrrolidone to give a 26% by weight solution. The light brown solution was added to the periodontal pocket of a greyhound dog. As soon as the solution came in contact with the tissue, a greyish precipitate formed. The precipitate was easily washed off the tissue with water. This experiment demonstrates the effect of the solution concentration on tissue penetration.

EXAMPLE 5

Chlorhexidine diacetate was dissolved in N-methyl-2-pyrrolidone to give a 5% by weight solution of drug. The solution was clear and colorless. When applied to human skin, the solution penetrated readily into the tissue with no visible evidence of residue on the surface of the skin. In other words, the drug penetrated into the tissue in a desirable manner.

EXAMPLE 6

Tetracycline hydrochloride was added to N-methyl-2-pyrrolidone to give a 5% by weight dispersion. Although a dispersion was formed initially, after standing overnight, the drug completely dissolved to give a light yellow solution. When the solution was applied to human skin, it readily absorbed into the tissue.

EXAMPLE 7

Tetracycline as the free base was added to N-methyl-2-pyrrolidone to give a 5% by weight solution. The drug dissolved readily into the solvent to give a light yellow solution. When the solution was applied to human skin, it absorbed quickly into the tissue.

EXAMPLE 8

The organic acid salts of sanguinarine including the gluconate, lactate, and acetate were prepared by dissolving the base form of sanguinarine in acetone and adding the appropriate acid such as gluconic, lactic, and glacial acetic acid to the solution in an equimolar concentration. The acetone is then removed by evaporation to give the solid organic acid salt of sanguinarine.

EXAMPLE 9

Sanguinarine gluconate was dissolved in N-methyl-2-pyrrolidone to give a 15% by weight solution. The reddish orange solution when applied to human skin penetrated readily into the tissue with no visual evidence of residue of the surface of the skin. The orange color at the site of application could not be removed by wiping or washing with water and was evident for about three days.

EXAMPLE 10

Sanguinarine lactate was dissolved in N-methyl-2-pyrrolidone to give a 10% by weight solution. The light yellow solution when applied to human skin penetrated readily into the tissue leaving no visible residue or color. After approximately 30 minutes, the area to which the solution has been applied turned an orange color which could not be removed from the skin by wiping or washing with water. The color was evident for about three days.

EXAMPLE 11

Sanguinarine acetate was dissolved in N-methyl-2-pyrrolidone to give a 5% by weight solution. The yellow solution when applied to human skin penetrated readily into the tissue with no visual evidence of residue on the surface of the skin. In about 30 minutes, the area to which the solution had been added turned an orange color. The orange color could not be removed from the skin by wiping or washing with water.

What is claimed is:

1. In a method for the treatment of a patient having periodontal disease by topically administering by supragingival solution irrigation into the periodontal pocket a pharmaceutical composition containing an antimicrobial agent to the patient's periodontal tissue surfaces that are infected with bacteria, wherein the improvement comprises the steps of:
   (1) combining a non-aqueous solution of a penetration enhancer which is a solvent for the antimicrobial agent with the pharmaceutical composition,
   (2) to carry the antimicrobial agent from the periodontal pocket into the internal region of the gingival tissue surrounding the periodontal pocket.

2. A method according to claim 1, wherein the antimicrobial agent is highly soluble in the penetration enhancer and sparingly soluble in water or body fluids, so that after the antimicrobial agent internally penetrates the periodontal tissue, it is deposited inside the periodontal tissue.

3. A method in accordance with claim 1 in which said penetration enhancer is selected from N-methyl-2-pyrrolidone, 2-pyrrolidone, propylene glycol, dimethylformamide, dimethyl sulfoxide, caprolactam, oleic acid, decylmethylsulfoxide, 1-dodecylazacycloheptan-2-one, isopropyl myristate, hexamethylene palmitamide, hexamethylene lauramide, and other aliphatic acids, and esters.

4. A method in accordance with claim 1 in which said antimicrobial agent is selected from tetracycline, chlorhexidine, metronidazole, minocycline, clindamycin, acetylsalicyclic acid, acetaminophen, ibuprofen, flurbiprofen, and ketanserin, and benzophenanthridine alkaloids which are soluble in said penetration enhancer.

5. A method in accordance with claim 1, wherein said agent is selected from the group consisting of ethoxydihydrosanguinarine, sanguinarine gluconate, sanguinarine lactate, sanguinarine acetate, chlorhexidine diacetate, chlorhexidine gluconate, tetracycline, and tetracycline hydrochloride; and wherein said penetration enhancer comprises N-methyl-2-pyrrolidone.

6. A method in accordance with claim 1, wherein said agent is present in said solution at a concentration of about 1 to 20% by weight.

7. A method in accordance with claim 4, wherein said agent is present in said solution at a concentration of about 1 to 20% by weight.

8. A method in accordance with claim 5, wherein said agent is present in said solution at a concentration of about 1 to 20% by weight.

* * * * *

UNITED STATES PATENT AND TRADEMARK OFFICE
CERTIFICATE OF CORRECTION

PATENT NO. : 4,975,271

DATED : December 4, 1990

INVENTOR(S) : Dunn et al.

It is certified that error appears in the above-identified patent and that said Letters Patent is hereby corrected as shown below:

On the title page, in item [54] and in column 1, in the title, "MUSCOSAL" should read --MUCOSAL--.

On the title page, in the ABSTRACT, line 1, "muscosal" should read --mucosal--.

In column 3, line 54, "destry" should read --destroy--.

Signed and Sealed this

Third Day of November, 1992

Attest:

DOUGLAS B. COMER

*Attesting Officer*   *Acting Commissioner of Patents and Trademarks*